United States Patent [19]

Gaylor et al.

[11] Patent Number: 5,048,766
[45] Date of Patent: Sep. 17, 1991

[54] APPARATUS AND METHOD FOR CONVERTING INFECTIOUS WASTE TO NON-INFECTIOUS WASTE

[76] Inventors: Michael J. Gaylor, 1978 Lynnwood Ct., Dunedin, Fla. 34698; John Hodges, 1412- 21 St., Palm Harbor, Fla. 34683

[21] Appl. No.: 529,081
[22] Filed: May 25, 1990
[51] Int. Cl.$^5$ .............................................. B02C 21/02
[52] U.S. Cl. ...................................... 241/65; 241/99; 241/101.7; 241/154; 241/DIG. 38
[58] Field of Search ........................ 241/23, 99, 29, 65, 241/154, 101.4, 3, 101.7, DIG. 38, 166

[56] References Cited

U.S. PATENT DOCUMENTS 2,731,208  1/1956  Dodd ............................... 241/166 X
3,589,276  6/1971  Swallert ............................ 241/99 X
4,884,756  12/1989  Pearson ............................. 241/99 X
4,905,916  3/1990  Sorwick et al. ................... 241/65 X Primary Examiner—Mark Rosenbaum
Attorney, Agent, or Firm—Joseph C. Mason, Jr.; Ronald E. Smith

[57] ABSTRACT

Infectious medical waste is rendered non-infectious by an apparatus that includes a hopper into which the infectious waste is charged, a pair of grinders or other destruction devices that reduce the waste materials to small particles, a first heating station where harmful life forms are destroyed and a cooling station where the ground and heated materials are cooled to a level safe for handling by conventional trash removal personnel. Sharps containers are cut apart by an externally mounted sharps container cutter that cuts the containers apart before they reach the grinders.

8 Claims, 2 Drawing Sheets

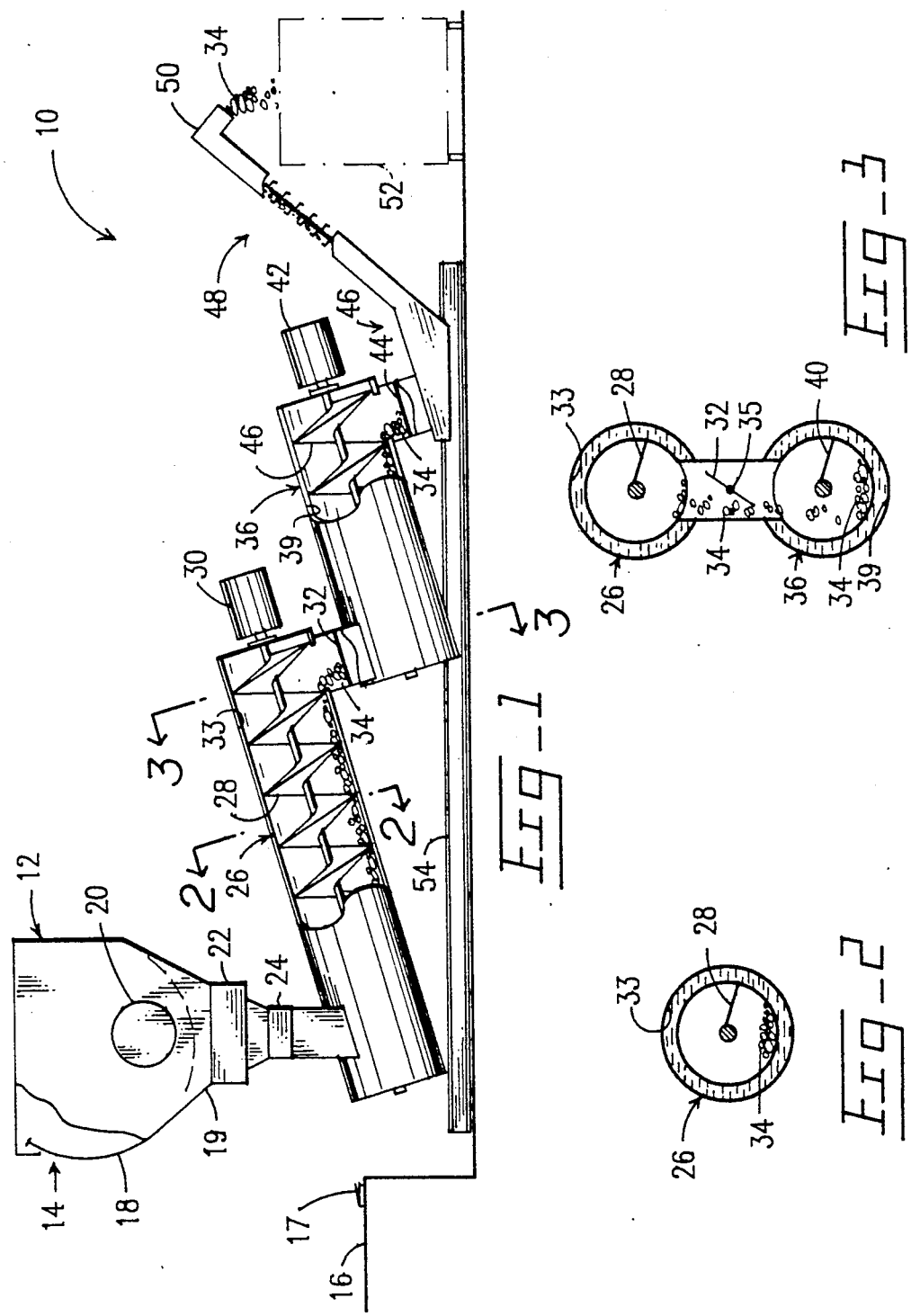

APPARATUS AND METHOD FOR CONVERTING INFECTIOUS WASTE TO NON-INFECTIOUS WASTE

TECHNICAL FIELD

This invention relates, generally, to a device that grinds and sterilizes medical waste to render it disposable as a non-infectious waste.

BACKGROUND ART

Materials that meet the definition of "infectious waste," as defined by the Environmental Protection Agency or the Center for Disease Control (Atlanta, Ga.), must be disposed of in a specified manner that renders it non-infectious. Steam sterilization, incineration, and other acceptable means must be employed. If the treatment process is off-site, i.e., at a location other than the site where the infectious waste was generated, then the waste must be packaged, transported, stored and otherwise handled in accordance with a multitude of strict regulations. Compliance with such regulations requires the increased expenditure of labor and other resources and accordingly is very costly vis a vis the cost of disposing of non-infectious wastes.

Most medical wastes easily qualify as infectious waste and thus require special handling. Hospitals generally place needles, syringes and other sharp objects in rigid, hard plastic cylindrical containers known as sharps containers. All other contaminated materials are placed in red plastic bags. Both the sharps container and the red bags require special handling and disposal. However, some producers of infectious waste cavalierly ignore applicable laws and dump such waste illegally, thereby despoiling the environment and threatening public health. The cleanup costs are paid by third parties unless the responsible parties are apprehended and compelled to pay by legal measures.

The quantity of medical waste produced each year is substantial; those hospitals and other facilities that generate large amounts of such waste are heavily burdened by the cost of legally disposing of the same and suffer unfair competition from those facilities that circumvent the laws.

Accordingly, there is a clear need for new solutions to the medical waste disposal problem. The old solution of disposing of such wastes at conventional, approved disposal sites having facilities for treating the waste is unacceptable due to its high cost, but the prior art neither teaches nor suggests how the unsatisfactory state of the art could be advanced.

DISCLOSURE OF THE INVENTION

The longstanding but heretofore unfulfilled need for a more cost effective way of handling medical waste is now fulfilled by a novel apparatus that is installed on the grounds of the facility generating the waste. The apparatus accepts medical waste in a hopper at a first end thereof and delivers trash classified as non-infectious waste at a second end thereof.

More particularly, items loaded into the hopper are first ground by a double grinder and rendered unrecognizable. Next, the ground material is slowly carried through a heating station where viruses, bacteria, spores and other microorganisms are killed. The hot, ground material is then carried slowly through a cooling station and is then deposited onto a conveyor means that transports it to a refuse collection station. The grinding and heating destroys dangerous objects such as hypodermic needles and harmful life forms, respectively, and the cooling enables the ground and sterilized material to be handled in the same manner as any other non-infectious waste.

The construction of the novel unit is inexpensive, and thus affordable by facilities that produce copious amounts of medical waste. The unit pays for itself within economically acceptable times in savings derived by avoiding the special handling fees required for infectious waste disposal.

It is therefore understood that the primary object of this invention is to provide a novel and cost effective method for converting infectious waste into non-infectious waste.

These and many other objects and advantages of this invention will become apparent a this description proceeds.

The invention accordingly comprises the features of construction, combination of elements and arrangement of parts that will be exemplified in the construction set forth hereinafter and the scope of the invention will be set forth in the claims.

DESCRIPTION OF THE DRAWINGS

For a fuller understanding of the nature and objects of the invention, reference should be made to the following detailed description, taken in connection with the accompanying drawings, in which:

FIG. 1 is a side elevational, diagrammatic view of an exemslary embodiment of the novel apparatus;

FIG. 2 is a sectional view taken along line 2—2 in FIG. 1;

FIG. 3 is a sectional view taken along line 3—3 in FIG. 1; and

BEST MODES FOR CARRYING OUT THE INVENTION

Figure 4:
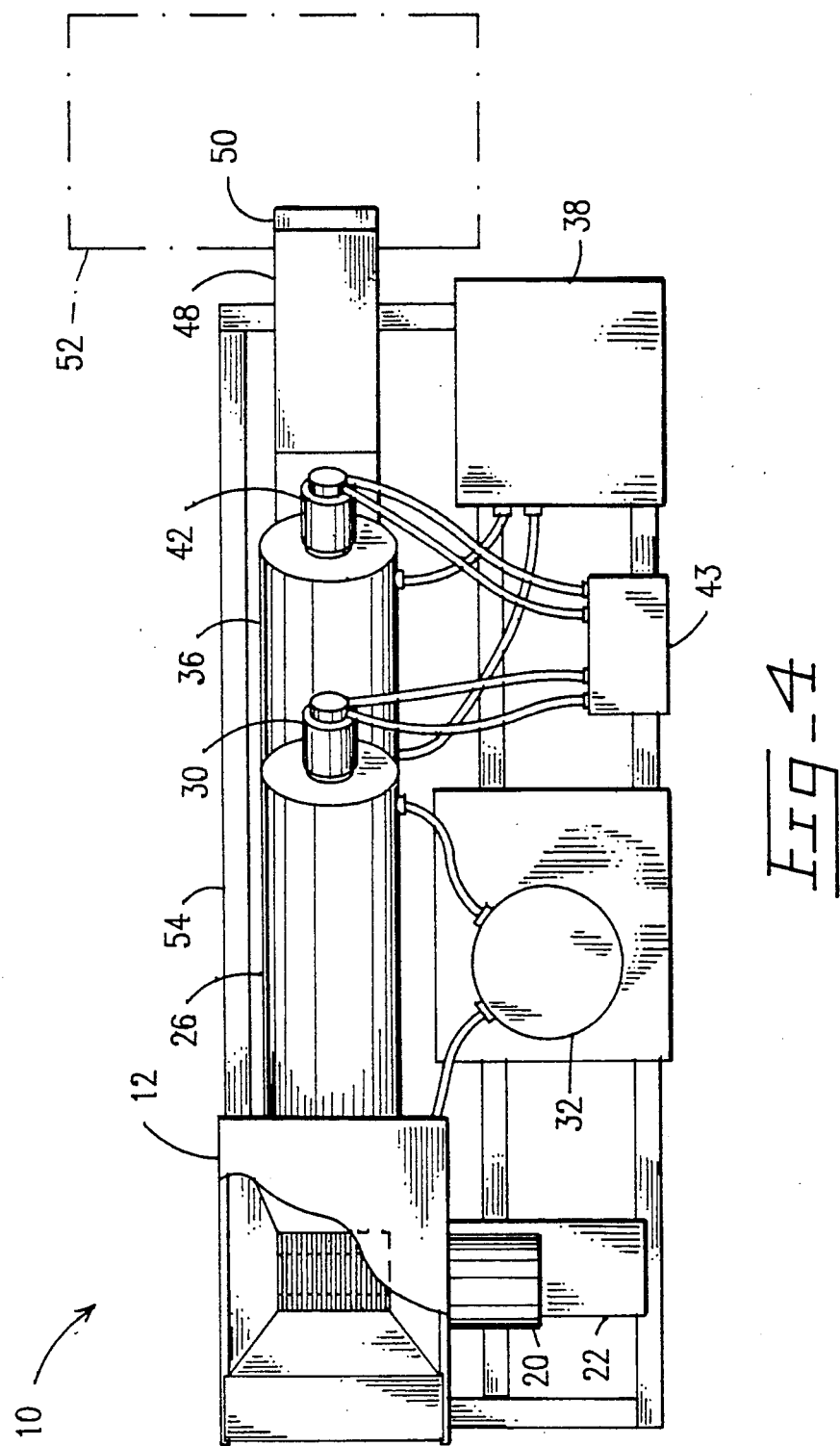
FIG. 4 is a top plan view thereof.

Referring now to FIG. 1, it will there be seen that an illustrative embodiment of the invention is denoted as a whole by the reference numeral 10.

Apparatus 10 includes hopper 12 having an access opening or charge port 14 positioned a convenient, accessible height above a floor 16 of a loading dock. Opening 14 is closed by a rotatably mounted motor operated door 18 having a semicircular construction as shown. A foot pedal 17 is used to open and close door 18.

A cutter 20 for cutting open or otherwise destroying the hard plastic sharps containers is positioned outside of hopper 12 as best understood in connection with FIG. 4. The individual in charge of disposing of the sharps containers must deposit them into cutter 20. The discharge end of cutter 20 is in open communication with the interior of hopper 12 as best shown in FIG. 4. Cutter 20 cuts the sharps containers into pieces, but does not thoroughly destroy the sharp objects therein.

A first grinder 22 is positioned below hopper 12 in downspout or discharge port 19 thereof and is gravity fed; it grinds into very small particles all materials deposited into hopper 12 and sharps cutter 20. (A hammermill would be a suitable substitute for grinder 22 in some situations). If cutter 20 were not employed, the cylindrical sharps container might simply roll atop grinder 22. The small particles exiting grinder 22 include the remains of the sharps container and its contents, which remains are gravity fed into a second grinder 24, positioned at the lowermost end of downspout 19 and are there ground into even smaller particles. Grinder 24 could also be a hammermill if design considerations suggested such. This double grinding insures the total physical disintegration of the medical waste materials and increases the total surface area thereof to thereby increase the effectiveness of the heat treatment to which said particles are subsequently exposed.

The double ground materials are then gravity fed into a first, charging end of housing or heat station 26. Housing 26 is disposed at a predetermined angle as shown and houses an elongate auger 28 therein that is slowly rotated about its longitudinal axis of symmetry by hydraulically operated motor 30.

In a preferred embodiment, the internal temperature of heat station 26 is maintained at 350 degrees Fahrenheit (162 degrees Celsius) by boiler 32 (FIG. 4), which may be a vertical tube boiler with a chemical feed or other suitable means. Heat transfer jacket or sleeve 33 encircles station 26 along its extent, as perhaps best understood in connection with FIGS. 2 and 3. The internal temperature of heat station 26 is continuously monitored by averaging a bulb thermometer with a chart recorder. No incineration occurs.

To insure the destruction of all viral and bacterial life forms, the rotation of the auger 28 is set at an angular velocity that insures that ground material entering housing 26 at its lowermost end will dwell within said housing for about sixty minutes.

Upon reaching the elevated, discharge end of auger 28, the ground and heated material falls, as depicted in FIG. 1, under the influence of gravity onto rotary air lock 32 which has a revolving door-like construction and which rotates about its axis of rotation 35 (FIG. 3) under the weight of ground material 34 deposited thereatop. As air lock 32 rotates, the material falls under the influence of gravity to the lowermost, first end of inclined housing 36. The interior of housing or cooling station 36 is cooled to approximately 130 degrees F. by suitable means such as cooling tower 38 (FIG. 4) and cooling sleeve 39. Inclined auger 40 is rotatably mounted interiorly of housing 36 and rotates as driven by hydraulically operated motor 42 at a predetermined angular velocity to insure that the ground materials are cooled to about 130 degrees F. by the time they attain the elevated, discharge end of said auger 40. Motors 30 and 42 are preferably driven by hydraulic power source 43, shown in FIG. 4; the motors could also be electrically, pneumatically, or otherwise driven.

The ground and cooled materials 34 that have substantially attained the uppermost end of auger 40 fall under the influence of gravity, as depicted, onto rotary airlock 44 that operates in the same way as air lock 32.

The material then falls onto the loading station 46 of an upperwardly inclined drag chain conveyor 48 that is enclosed for aesthetic and safety reasons. Materials arriving at the top 50 thereof fall under the influence of gravity into a suitable dumpster 52.

Advantageously, the entire apparatus 10 is mounted on an elongate skid beam 54. The breadth of the skid beam 54 is such that apparatus 10 is transportable over public highways; in the embodiment shown, the breadth is about seven and one-half feet. Moreover, suitable interlock means, not shown, are provided to disable the grinders and the sharps cutter when door 18 is opened.

It should therefore be clear that the novel method includes the steps of charging sharps containers into a sharps cutter and all other medical waste into a hopper having a downspout, cutting into pieces said sharps container, grinding for a first time all objects charged into the hopper and said cutter, grinding for a second time all of said objects to insure that all of said objects have been reduced to small particles, introducing the cut and double ground articles into a heat station having a predetermined elevated temperature, conveying the particles through said heat station at a slow rate of speed so that said particles dwell within the heat station for about an hour, cooling said particles and discharging the cooled particles into a collection space for non-infectious materials. The method results in no discharge of pollutants into the air or sewer system.

Clearly, this invention is new and useful. Moreover, it was not obvious to those of ordinary skill in this art at the time it was made, in view of the prior art, considered as a whole.

This invention pioneers the art of converting infectious medical wastes into non-infectious waste. Therefore, the claims that follow are to be broadly interpreted and enforced so as to protect the heart of this major invention, as required by law.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention which, as a matter of language, might be said to fall therebetween.

Now that the invention has been described,
What is claimed is:

1. An apparatus for converting infectious waste into non-infectious waste, comprising:
    a hopper for receiving waste materials;
    said hopper having a charge port and a discharge port;
    a first grinder member positioned below said discharge port so that waste materials charged into said hopper fall into said first grinder member under the influence of gravity;
    a heating station having a predetermined internal temperature;
    boiler means for maintaining said predetermined internal temperature of said heating station;
    said heating station having an elongate construction and being upwardly inclined at a predetermined angle from a first end thereof to a second end thereof, said second end being higher than said first end;
    said first end of said heating station being positioned in open communication with a discharge port of said first grinder member;
    a cooling station having a predetermined internal temperature substantially less than the internal temperature of the heating station;
    means for maintaining said predetermined internal temperature of said cooling station;
    said cooling station having an elongate construction and being upwardly inclined at a predetermined angle from a first end thereof to a second end thereof, said second end being higher than said first end;

an air lock means positioned between said second end of said heating station and said first end of said cooling station;

said second end of said heating station, said air lock means, and said first end of said cooling station being disposed in substantially vertical relation with respect to one another;

a first rotatably mounted auger member positioned within said heating station, rotation of said first auger member being operative to carry waste materials from said first end of said heating station to said second end of said heating station;

a second rotatably mounted auger member positioned within said cooling station, rotation of said second auger member being operative to carry waste materials from said first end of said cooling station to said second end of said cooling station;

said predetermined internal temperature of said heating station being sufficient to destroy infectious life forms;

said predetermined internal temperature of said cooling station being sufficient to cool waste materials to a temperature where said waste materials are safe to handle in the absence of special material handling means; and said heating station and said cooling station being disposed in longitudinal alignment with one another to minimize the width of said apparatus so that it is transportable over public highways.

2. The apparatus of claim 1, wherein said heating station and said cooling station are disposed at a common angle of inclination relative to a horizontal plane.

3. The apparatus of claim 2, wherein said air lock means is a rotary air lock, and wherein said rotary air lock has an axis of rotation disposed at said common angle.

4. The apparatus of claim 3, further comprising a second air lock means positioned at said second end of said cooling station, said second air lock means being a second rotary air lock having an axis of rotation disposed at said common angle.

5. The apparatus of claim 4, further comprising a second grinder member positioned in vertical alignment with said first grinder member in open communication therewith, said second grinder member being positioned below said first grinder member, being gravity fed, and being positioned above said first end of said heating station in open communication therewith.

6. The apparatus of claim 5, further comprising a sharps cutter positioned adjacent said hopper, said sharps cutter having a discharge port in open communication with an interior of said hopper so that materials discharged by said sharps cutter enter into said hopper and thence into said first and second grinder members, in succession.

7. The apparatus of claim 6, further comprising a discharge conveyor means having a first, lower end positioned below said second end of said cooling station and a second, elevated end remote therefrom, said first end of said discharge conveyor means being in open communication with said second end of said cooling station, through said rotary air lock, and said second end of said discharge conveyor means being in open communication with a waste collection means of the type into which should be deposited only non-hazardous wastes.

8. The apparatus of claim 7, further comprising an elongate, flat skid beam member upon which is mounted said hopper, said heating station, said cooling station and said discharge conveyor means, said skid beam having a predetermined breadth that permits its conveyance over public highways.

* * * * *